(12) United States Patent
Jones et al.

(10) Patent No.: US 6,355,624 B1
(45) Date of Patent: Mar. 12, 2002

(54) MEASUREMENT OF PLASMA VOLUME (75) Inventors: John Gareth Jones; Frederick Stephen Wusteman, both of Cardiff; Charles Alexander James Wardrop, Scotland, all of (GB)

(73) Assignees: University Wales College of Medicine; University of Wales, Cardiff, both of Cardiff (GB)

( * ) Notice: Subject to any disclaimer, the term of this patent is extended or adjusted under 35 U.S.C. 154(b) by 0 days.

(21) Appl. No.: 09/355,882

(22) PCT Filed: Feb. 5, 1998

(86) PCT No.: PCT/GB98/00362

§ 371 Date: Oct. 15, 1999

§ 102(e) Date: Oct. 15, 1999

(87) PCT Pub. No.: WO98/35230

PCT Pub. Date: Aug. 13, 1998

(30) Foreign Application Priority Data

Feb. 5, 1997 (GB) ............................................... 9702285
Dec. 19, 1997 (GB) ............................................... 9726795

(51) Int. Cl.$^7$ ...................... A01N 43/04; A61K 31/715; A61K 49/00; A61B 6/00
(52) U.S. Cl. ............................. 514/54; 514/59; 514/60; 424/9.1; 600/431
(58) Field of Search ........................... 128/654; 514/60, 514/59, 54; 600/431; 424/9.1

(56) References Cited

U.S. PATENT DOCUMENTS

| | | |
|---|---|---|
| 4,994,444 A | 2/1991 | Zikria |
| 5,024,231 A | 6/1991 | Feldschuh et al. |
| 5,685,302 A | 11/1997 | Zikria et al. |

FOREIGN PATENT DOCUMENTS

| | | |
|---|---|---|
| WO | WO 95/15721 | 5/1996 |
| WO | WO 96/16588 | 5/1996 |

*Primary Examiner*—Ralph Gitomer
*Assistant Examiner*—Mahreen Chaudhry
(74) *Attorney, Agent, or Firm*—Young & Thompson (57) ABSTRACT

A method of determining the presence or onset of capillary leakage includes introducing into the blood stream of the subject a first low dosage of a low molecular weight macromolecular material and determining the volume of distribution thereof (an apparent volume of distribution). The determined value of volume of distribution is influenced not only by extravasation through the capillary wall but also by binding of smaller molecules to pores or receptor binding sites in the wall which occurs much faster than extravasation and is an important indicator of the onset of capillary leakage. The process is repeated with a high dose of high molecular weight macromolecular material to determine a further volume of distribution (the true circulating plasma volume). The two values are compared to determine the presence or onset of capillary leakage.

18 Claims, 1 Drawing Sheet

FIGURE 1

MEASUREMENT OF PLASMA VOLUME

This invention relates to methods for measuring the plasma volume of a human or animal and to compounds for use in such methods.

The adequate oxygenation of tissue depends on cardiac output, the concentration of haemoglobin and total circulating blood volume (BV). The concentration of haemoglobin is often expressed as the Haematocrit (Hct) or packed cell volume (PCV). At a given cardiac output, both haematocrit and total circulating blood volume are important determinants of tissue oxygenation. A low haematocrit means a low oxygen carrying capacity and a low blood volume leads to under perfusion of some tissue in order to maintain the oxygenation of others such as brain and cardiac muscle. The estimation of blood volume is therefore an important measurement in patients with threatened tissue oxygenation. Total blood volume (BV) is the sum of red cell volume (RCV) and plasma volume (PV) and they are related to the whole body haematocrit (Hct) by the following relationship:

$$Hct = \frac{RCV}{PV + RCV} = \frac{RCV}{BV} \qquad \text{Equation (1)}$$

It is known to assess the plasma volume (and thus indirectly the blood volume) using the plasma protein, albumin. Albumin has been labelled with various dyes, including Evans Blue (T1824) and Indocyanin Green, as well as being radio-labeled with iodine. A known amount of the labelled albumin is injected into the bloodstream and then a dilution analysis technique used to determine the volume of distribution of albumin. However, we have noted that, especially in sick patients, equating the volume of distribution of albumin to plasma volume is unsatisfactory in that the albumin also equilibrates into Interstitial water and also "leaks" at a rate of about 5% per hour and increasing to 15% per hour in patients with septic shock. The albumin space exceeds true plasma volume and this is exaggerated when capillary integrity is impaired. The "excess" volume of distribution of labelled albumin reflects mainly extravasation of the albumin simultaneously with its equilibration in the plasma in the circulation, in critically ill patients.

Accordingly, in present hospital practice worldwide, surgical resuscitation after blood loss is managed without accurate knowledge of measured blood volume. Likewise, intensive care patients who are dependant on respiratory support are managed without accurate knowledge of blood volume, but instead surrogate indicators of blood volume may be used such as clinical appraisal and intravascular pressure and flow measurements. These are only very generally related to the amount of blood in the circulation and it is possible for sick patients, including surgical cases or victims of trauma and the newborn, to have a deficiency of more than half the blood in their circulation.

Without any realistic possibility of routine measurement of plasma volume and thus total circulating blood volume, the effects of intravenous infusions used to attempt correction are hard to assess. Lack of this information seriously limits clinical monitoring and appraisal of the circulation of the most critically ill patients, as well as of less seriously sick patients who have undergone elective surgery.

The consequences of lack of knowledge of the circulating blood volume include management of patients who are hypo-volaemic with adverse effects on lung function and gastrointestinal tract, hepatic and renal perfusion by blood. In our own experience and observation, hypo-volaemia is extremely widespread in critically ill patients and goes undetected by present means of clinical evaluation and laboratory measurement.

Other methods of blood volume measurement are available which require the use of radioactive isotopes or non-radioactive "labels" to determine the amount of red cells and plasma in the circulation. Such methods include measuring red cells by monitoring dilution of cells labelled with radioactive chromium or technetium, or with non-radioactive biotin. Plasma is routinely measured from dilution of radiolabelled albumin. All of these measurements are expensive in expertise, time and financial cost and they do not lend themselves to widescale application. Furthermore, most of the standard methods are unsuitable for use in women in the childbearing age group or in children.

Accordingly, there is a need for a method of blood volume assessment with a more widely applicable and speedy methodology, which is less prone to error in critically ill patients and which can be implemented at relatively low cost and for 24 hours every day. Whilst the traditional methods of blood volume measurement using radiolabelled albumin are reasonably accurate in healthy patients, as noted above we have found that the accuracy declines considerably in sick patients, who are usually in most need of accurate blood volume measurement.

We describe below methods of determining the plasma volume of a human or animal, which methods comprise introducing into the bloodstream of the human or animal, labelled material comprising a modified or unmodified starch, or derivatives or mixtures thereof, and thereafter determining the concentration of said labelled material, thereby to determine the plasma volume.

In the course of our experiments we have found that, in sick patients, the plasma volume determined by use of labelled albumin is higher than that using labelled starches of somewhat larger molecular size We believe that this is due to the increased capillary permeability in sick patients arising from damage to the vascular endothelium, with albumin extravasating into the interstitial space which accounts for about 25% of the water volume of a normal adult. This has severe implications not only for the accuracy of any measurements of plasma volume using labelled albumin, but also for the use of albumin as a volume expander in patients undergoing major surgical procedures. A rapid and profound increase in systemic capillary permeability is now known to accompany all acute inflammatory states including major surgery, ischaemia and reperfusion injury, trauma, thermal injury, bacteraemia, and acute pancreatitis.

The problem with albumin infusion as a volume therapy stems from the ease with which albumin moves from the vascular compartment to the interstitium, even in health, and the loss of vascular endothelial integrity in disease. Of the 275 grams of albumin in a normal adult, 60% is to be found in the interstitial space, with 5 grams or more every hour moving across the normal vascular endothelium. This rate of leakage dramatically increases in any severe inflammatory condition leading to hypoalbuminaemia and interstitial oedema. Intravenous infusions of albumin, given in an attempt to correct blood loss during an acute inflammatory episode such as trauma, major surgery or their complications, are not only ineffective because albumin rapidly leaks out of the vascular compartment, but also worsen interstitial oedema, with each gram of albumin 'binding' 18 grams of water. The blood in the underfilled circulation, depleted of plasma and red blood cells, gives misleadingly 'normal' haemoglobin and haematocrit values, suggesting that red blood cell replacement has been adequate even though may be a deficit of up to 20–30% and typically 1.5–2.5 litres in an adult patient. The interstitial oedema and the inadequate red cell mass compromise both pulmonary gas exchange and tissue oxygen delivery. Hypovolaemia leads to reflex vasoconstriction, and splanchnic ischaemia, risking bacterial translocation and ineffective function of the reticuloendothelial system.

This clinic 'ITU' (Intensive Therapy Unit) syndrome of 'symmetrical' red cell and plasma depletion with hypovolaemia, hypoalbuminaemia and interstitial oedema yet normal haematocrit and haemoglobin is clinically unrecognizable until its late stages which may herald organ failures. Conventional management of hypovolaemia advocating albumin infusions without blood transfusion does not provide a sustained increase in intravascular volume since, in the 'sick' ITU patient with damaged vascular endothelium, albumin rapidly moves out of the vascular compartment and exacerbates interstitial oedema, especially in the lungs, gastrointestinal tract wall, kidneys and skin. Recognition of the failure of the vascular endothelium and the reduced blood volume should highlight the need for transfusion of red blood cells together with colloids which remain in the vascular compartment even during periods of capillary leak.

Furthermore, recent work by Gosling et al (Gosling P., Bascom J. V., Zikria, B. A, Capillary Leak, Oedema and Organ Failure; breaking the triad; Care of the Critically Ill 1996: 191–197) shows that capillary leak is of prime importance in the development of systemic inflammatory response syndrome (SIRS) and multiple system organ failure (MSOF) and that its early detection should allow its correction through replacement of deficient red cells and plasma.

Accordingly there is a need for a method of determining the capillary leakage of a patient, which can be effected easily and rapidly.

International Patent Application WO 96/15721 describes a method for determining plasma volume in which labelled macromolecules stated to be larger than the endothelial junctions in the patient's capillaries are introduced into the patient's blood stream and a dilution analysis carried out. However it will be noted from FIG. 1 of the document that the concentration of the macromolecular material reduces to around 70% of the starting value which indicates that the method would lack accuracy and that a proportion of the molecules supposed to remain in circulation are escaping.

International Patent Application WO 96/16588 describes a method for determining the presence of capillary leak in which a tracer material having molecules smaller than epithelial gaps in he capillary of a patient is introduced into the patient's blood stream and blood samples taken at intervals to ascertain the change in concentration of the tracer material with time over a time period from 30 minutes to 150 minutes. This method implies that capillary leakage can be determined by looking for differences in the rate of removal.

However our own data indicate that, over extended periods, the rate of removal of a polydisperse substance such a hydroxyethyl starch is independent of the molecular weight and of the presence or otherwise of capillary leakage, and therefore that this method would not be effective. In addition, the above disclosures apparently assume a one stage model in which the capillary vessels have gaps through which the smaller molecules may pass in an irreversible capillary leak.

The experiments below have led us to conclude that the mechanism is actually rather more complex, involving two different mechanisms. In a first stage molecules of smaller size are adsorbed into the capillary wall (for example by the smaller molecules binding to receptors or occupying pores). During this first stage (typically within the first 10 minutes), the concentration declines very quickly and the amount of the tracer material removed is dependent on the dose, the molecular size of the tracer materials and the presence of tissue oedema. We believe that the amount of tracer material removed in this way indicates the level of inflammation) capillary permeability, and is greater with small molecules and during endotoxaemia. This phenomenon is exemplified by an increase in the binding of small molecules to endothelial cell walls and/or a small increase in the number and/or size of the pores.

In the second stage, there are gross changes in pore size and density, and the molecules undergo a reversible equilibration between plasma and interstitial water, and the decline in concentration during the first hour or so represents this process.

The method of International Patent Application WO 96/16588 apparently assumes that the tracer macromolecules are either in circulation in the plasma or have leaked from the capillary into the interstitial space. However, this does not allow for molecules which become adsorbed into the capillary wall during the first stage, which we have found is an extremely important indicator of the onset of the stage two of the process, i.e. capillary leak syndrome. Thus tests such as that of International Patent Application WO 96/16588 do not indicate capillary leak until it has actually occurred, when it may be too late to save the patient.

Accordingly, methods which provide an early indicator of the onset of capillary leak during stage one could considerably improve patient treatment, by early transfusion of red blood cells as appropriate.

Thus the preferred embodiments below provide two estimates of the plasma volume; a first estimate using a low dose, low molecular weight tracer which gives an apparent volume of plasma distribution which varies according to the extent of adsorption of tracer molecules in receptor binding sites or small pores (and also leakage from the capillary), and a second estimate using a high dose high molecular weight tracer which gives a true plasma volume which is independent of surface adsorption and leakage effects. By comparing these two volumes a measure of capillary permeability is obtained which will flag the onset of capillary permeability indicated by increased surface adsorption etc., before the second stage occurs.

In one aspect, this invention provides a method of determining the presence or onset of capillary permeability of a subject which comprises:

introducing into the blood stream of the subject a dose of a first labelled macromolecular material;

taking at least one blood sample after said introduction;

determining the amount and/or concentration of said first labelled macromolecular material;

introducing into the bloodstream of the subject a dose of a second labelled macromolecular material having a relatively high molecular weight;

taking at least one blood sample after said introduction;

determining the amount and/or concentration of said second labelled high molecular weight macromolecular material;

using the relative determined concentrations and/or amounts of said labelled materials to indicate the presence or onset of capillary leakage.

Preferably, said low molecular weight tracer material and said high molecular weight tracer material comprise physiologically acceptable colloid or crystalloid materials, wherein, in humans or animals exhibiting capillary permeability, substantially all of said high molecular weight material remains within the capillary, whereas a substantial proportion of said low molecular weight material is capable of extravasation from plasma or adsorption on the capillary wall. Said low and high molecular weight materials may each comprise modified or unmodified polysaccharide. A particularly preferred material comprises hydroxyethyl starch which has already been cleared for clinical use as a plasma substitute or expander.

Hydroxyethyl starch has a branched and highly hydrated structure which makes it larger than other molecules of similar molecular mass. Preferably, said starch is polydisperse, with a weight-average molecular weight [$MW_w$], expressed in Daltons (Da), between about 200,000 and 450,000 and a number-average molecular weight [$MW_n$] between about 60,000 and 70,000 with $MW_w$ and $MW_n$ towards the lower ends of the ranges being particularly preferred. $MW_w$ is analogous to the mean of all molecular weights and is therefore influenced by the weight of large molecules. $MW_n$ is analogous to the median and is not influenced by a small proportion of very large molecules. A suitable material is 6% Elohaes™ available from Fresenius (UK) Limited in Chester, UK.

Said low and high molecular weight materials advantageously comprise respective low and high molecular weight fractions of a polydisperse colloid or crystalloid material.

Preferably said low molecular weight tracer material contains a substantial proportion of molecules of molecular weight less than 100,000, and said high molecular tracer material contains a substantial proportion of molecules having a molecular weight greater than 100,000.

Although various marking or labelling techniques may be used, said low and high molecular weight tracer materials preferably each include a fluorescent label, for example fluorescein isothiocyanate. To allow use of the same or similar labels and to reduce the time between introducing said materials, without the first test masking the results of the second, said low molecular weight tracer material is preferably introduced at a relatively low concentration, and said high molecular weight tracer materials is introduced at a relatively high concentration after the first sample has been taken, thereby to distinguish between said low and high molecular weight tracer materials.

Alternatively the labels of said low and high molecular weight materials may be different and mutually distinguishable, whereby said low and high molecular weight tracer materials may be introduced together into the bloodstream.

The invention also extends to a kit for use in a method as described above, the kit comprising:
(i) a container containing a low molecular weight labelled tracer material having a relatively low molecular weight, and
(ii) a container containing a high molecular weight labelled tracer material having a relatively high molecular weight.

Said high molecular weight material preferably comprises a high molecular weight fraction of a polydisperse starch, said fraction containing a substantial proportion of molecules having a molecular weight of greater than 100,000, and said low molecular weight material comprises a low molecular weight fraction of said polydisperse starch, said fraction containing a substantial proportion of molecules with a molecular weight of less than 100,000.

Whilst the invention has been described above, it extends to any inventive combination of the features set out above or in the following examples.

The examples are given for illustration only and are not intended to limit the scope of the invention in any way,

EXAMPLE 1

Preparation of Fluorescein Isotuiocyanate (FITC) Labelled Hydroxyethyl Starch (HES) (FITC-Elohaes™)

(i) Coupling of Putrescine to Elohaes™

Putrescine dihydrochloride (4.0 g obtained from Sigma Chemical Company was dissolved in 100 ml of Elohaes™ (a 6% colloidal solution in physiological saline of hydroxyethyl starch having an average molecular weight $M_w$, of 200,000, and a degree of substitution 0.62, obtained from Fresenius (UK) Limited), and the pH was adjusted to 7.0 with a small volume of 1M NaOH Borane pyridine complex (1 ml) obtained from Sigma Chemical Company was added (with care, in a fume cupboard) and the mixture sealed and left in the dark at room temperature (with occasional vigourous agitation) for 14 days. Ethanol (300 ml) was then added, with constant swirling, and the mixture left overnight at 4° C. to ensure complete precipitation. The precipitate was collected by centrifugation at 1500 r.p.m. for 15 minutes. Traces of unbound putrescine are removed by re-dissolving the precipitate in a minimum volume of water (approx. 50 ml) and repeated precipitation of the polysaccharide with three volumes of ethanol. Centrifugation was carried out again to collect the precipitate. Repeated precipitation and centrifugation was continued until the ethanol fails to form a visible precipitate (4 or 5 times). A small volume of ethanol, saturated with sodium acetate trihydrate, was then added to help the precipitate to form. The mixture was continuously stirred until the precipitate was of a powdery consistency. This precipitate is then washed into a No. 3 sintered glass funnel (not under suction), washing sequentially with clean ethanol, acetone and ether. The resulting fine white powder was allowed to dry in a gentle current of air in a fume cupboard.

(ii) Determination of Free Amino Residues

It is important to ensure that the final product be devoid of free putrescine and this was verified by measuring the concentration of amino groups. In a solution containing 1 mg/ml of the modified starch, the maximum concentration of amino groups should be 5 $\mu$M or 17 $\mu$M for polysaccharides with a mass of 200,000 and 60,000 Daltons respectively. For practical purposes the preparation is not considered suitable if the measured concentration of free amino groups is in excess of 1.0 M. The free amino groups were assayed as described below.

A 10.0 g/l aqueous solution of Putrescine-Elohaes™ (1.0 ml) was added to 2.0 ml of 0.5M phosphate buffer (pH 8.0) and 2.0 ml of a 1.0 g/l aqueous solution of 2,4,6-Trinitrobenzene-sulphonic acid. The reaction mixture was incubated at 40° C. for approximately 90 minutes, then subsequently treated with 1.0 ml of 6M HCl to terminate the reaction. The absorbance of the resulting faint yellow solution was read at 348 nm.

Water substituted the test sample for the blank and 0.2 mM Putrescine dihydrochloride was employed as the standard solution.

(iii) Dialysis—to Remove Persistence Traces of Putrescine

If the free amino residue concentration is greater than 10 μM, large scale dialysis is carried out to remove persistent traces of Putrescine. The Putrescine-Elohaes™ powder is dissolved in a minimum amount of water (100–200ml). Dialysis tubing is soaked in water for a few hours and then rinsed thoroughly with clean water, secured by tightly knotting one end. The Putrescine-Elohaes™ solution is then dialysed against approximately 5 litres of water for 24 hours. The water is then exchanged for clean water and dialysis continued for a further 24 hours. A free amino residue determination can then be carried out on the dialysate to evaluate the ratio of Putrescine molecules to free reducing ends of polysaccharide chains.

(iv) Synthesis of FITC Conjugate of Putrescine-linked Elohaes™

A small amount of di-sodium tetraborate is added to the Putrescine-Elohaes™ dialysate, to give a saturated aqueous borax solution (approx. pH 9.0). Fluorescein isothiocynate isomer-1 (FITC), (available from Fisher Scientific), (200 mg per 4.0 g of Putrescine-Elohaes™) is then added quickly. The mixture is sealed, shaken thoroughly and left isolated from light for two days. The FITC-Elohaes™ conjugate is then recovered by repeated dissolving and re-precipitation, as for the Putrescine-Elohaes™ complex, with three volumes of ethanol. This process of repeated precipitation is continued until the precipitation with sodium acetate trihydrate saturated ethanol yields a powdery precipitate. The precipitate is then washed into a No. 3 sintered glass funnel as before, washing sequentially with clean ethanol, acetone and finally ether. The resultant fine yellow-orange powder is dried in a gentle current of air in a fume cupboard.

Determination of the presence of unbound FITC molecules is carried out by gel chromatography. A Sephadex G-200 column (Pharmacia Biosystem) (1.25 cm×15 cm) is employed with a 0.5 ml sample of FITC-Elohaes™ being eluted with water. Only one peak should emerge, representing the derivatised polysaccharide. Further separation may be required if more than one peak emerges.

(v) Separation of Unbound Traces of FITC FROM FITC-Elohaes™

Persistent traces of unbound FITC molecules are removed by a larger scale separation using a Sephadex G-25 column (2.4 cm×2.5 cm). A 3.0 ml sample of FITC-Elohaes™ is again eluted with water. The main peak eluting first represents FITC-Elohaes™ and is retained. The minor peak eluting towards the end of the column volume represents unattached molecules of FITC. Alternatively, the unbound FITC molecules may be removed by dialysis. Separation by dialysis provided a means of refining the whole preparation of FITC-Elohaes™ in one step. The yellow/orange powder of FITC-Elohaes™ was dissolved in a minimum amount of distilled water (30–50 ml). Pre-soaked dialysis tubing was rinsed thoroughly with clean distilled water and secured by knotting one end. The polysaccharide preparation was dialysed again approximately 5 litres of distilled water for 48 hours, the water being exchanged for clean water every 12 hours. When gel permeation chromatography, as described above, revealed only one peak then the preparation of FITC-Elohaes™ was precipitated with ethanol as before the final product being a fluorescent polysaccharide free from traces of unattached FITC molecules.

EXAMPLE 2

The volume of distribution of FITC-Elohaes™ was compared to albumin labelled with Evans Blue in healthy rabbits. For the FITC-Elohaes™ data, FITC-Elohaes™ powder was dissolved in isotonic saline to give concentrations in vivo from 0.15 mg to 17.0 mg per kg body weight of the rabbit. The highest dose of 17 mg/kg was composed of 2.0 mg/kg of FITC-Elohaes™ and the overall concentration made up by Elohaes™. The different amounts of FITC-Elohaes™ were administered to a total of 5 rabbits as described in the procedure below.

All rabbits used were adults of either sex, weighing approximately 3 kg. Both ears of the rabbit were first anaesthetised by topical application of Elma cream about 30 minutes prior to commencement of the procedure. A small cut was made into the left ear vein, using a scalpel, to enable relatively simple blood sampling. A sample of blood (approximately 1.0 ml) was obtained from the cut ear vein and collected into tubes coated with anti-coagulant (EDTA). FITC-Elohaes™ was then injected into the opposite ear vein and the time of injection noted. A mixing time of at least 5 minutes was allowed before blood sampling began. Blood samples ($\approx 1.0$ ml) were then withdrawn at various time intervals following injection, up to a maximum of 2 days. Most samples were collected within the first 3 hours and no more than 9 post-injection blood samples were taken from each rabbit. The blood samples were then centrifuged {Centaur 2} at 2300 r.p.m. for 10–15 minutes and the plasma withdrawn.

To estimate the volume of distribution of FITC-Elohaes™, plasma (0.25 ml) was made up to 1.0 ml distilled water (0.75 ml) and 2.0 ml of borate buffer (0.067M; pH 10,0) was then added and the fluorescence measured using a Perkin-Elmer LS-5 luminescence spectrometer, and quoted per ml of solution. The concentration of FITC-Elohaes™ was estimated, in all samples, from the fluorescence, and the volume of distribution of FITC-Elohaes™ was estimated by fitting the data to a suitable pharmacokinetic model.

Values for rate constants in mathematical models, as well as the volume of distribution of FITC-Elohaes™ were obtained by minimisation of the squares of deviations of experimental values from theoretical values predicted by an appropriate equation. The minimisation procedure was obtained from the NAG library {Numerical Algorithms Group, Oxford; Routine E04FCF:NAGFLIB:1652/0: Mk7: December 1978}. This routine was called by a programme, written by the user and incorporated a subroutine with the appropriate mathematical equation. The NAG routine also returns elements of the Jacobian matrix which were used for computing the variances of the derived constants.

For mathematical models comprising differential equations, the theoretical curve was computed by numerical integration using routine D02BBF {NAGFLIB:1564/0: Mk7: December 1978}. These computer programmes were written in FORTRAN and are capable of analysing any number of experimental curves with results placed in a table suitable for entry into MINITAB for statistical analysis. However, the chosen numerical integration method was a Runga-Kutta-Merson method, which did fail for some experimental curves. In these cases a more robust method of integration was chosen. This is the Episode method for stiff systems and available from Scientist™ {(Micrometh Scientific Software, PO Box 21550, Salt Lake City, Utah 84121, USA} as part of a general curve-fitting software package.

The volume of distribution is of FITC-Elohaes™ calculated from the degree of dilution of FITC-Elohaes™ in the plasma at the time of injection. The data have been fitted to a mono-exponential, bi-exponential and tri-exponential kinetic model. The bi-exponential model is chosen, on the basis of an F-test, as the least complicated acceptable model. The data were thus fitted to the following equation:

$$[\text{FITC-ELOHES}] = C_1 e^{-\lambda_1 t} + C_2 e^{-\lambda_2 t}$$

Where $C_1$, $C_2$, $\lambda_1$ and $\lambda_2$ are constants and the volume of distribution is given by $$V_d = \frac{DOSE}{(C_1 + C_2)}$$

For the Evans Blue data, a solution of Evans Blue {0.8 mg/ml} was prepared and administered to rabbits at a dose of 0.2 mg/ml (see El-Sayed H, Goodall S R Hainsworth R(1995). Re-evaluation of Evans Blue dye dilution method of plasma volume measurement), following the same procedure as for FITC-Elohaes™. Blood samples were withdrawn at 5, 10 and 20 minutes following injection, into tubes which were free from any anticoagulant. The blood was allowed to clot for about two hours and then centrifuged at 2500 r.p.m. for 10–15 minutes. The serum was removed and, in the absence of any visible signs of haemolysis, the absorbance measured at 610 nm. the procedure was calibrated by adding known amounts of Evans Blue to serum in vitro.

The volume of distribution of Evans Blue was determined by plotting the log, values of the first three points against time and linear regression analysis gave the line of least squares fit. The concentration of Evans Blue in serum at time zero was derived by reverse extrapolation. Thus, the volume of distribution was calculated from the degree of dilution (El-Sayed et al., 1995).

Table 1 shows the results for FITC-Elohaes™ and Table 2 showing the results for Evans Blue. It was found that the volume of distribution of the polysaccharide (44.5 ml/kg) was significantly lower than that of the albumin (53.1 ml/kg) (p=0.0006).

DATA RABBITS

TABLE 1

Plasma volume estimations in five rabbits using FITC-Elohaes

| Rabbit | Plasma Volume (ml) | Weight (Kg) | Plasma Volume (ml/Kg) |
|---|---|---|---|
| 1 | 112.26 | 2.553 | 43.97 |
| 2 | 121.97 | 2.600 | 46.90 |
| 3 | 135.04 | 3.000 | 45.01 |
| 4 | 156.49 | 3.402 | 46.03 |
| 5 | 180.49 | 4.450 | 40.56 |
| Mean | 141.25 | 3.201 | 44.49 |
| SD | ±27.49 | ±0.78 | ±2.46 |

TABLE 2

Plasma volume estimations in four rabbits using Evans Blue

| Rabbit | Plasma Volume (ml) | Weight (Kg) | Plasma Volume (ml/Kg) |
|---|---|---|---|
| 1 | 179.95 | 3.430 | 52.46 |
| 2 | 132.96 | 2.600 | 52.55 |
| 3 | 161.30 | 2.900 | 55.62 |
| 4 | 155.45 | 3.008 | 51.68 |
| Mean | 157.42 | 2.985 | 53.08 |
| SD | ±19.36 | ±0.344 | ±1.74 |

EXAMPLE 3

The volume of distribution of FITC-Elohaes™ was compared with that of Evans Blue labelled albumin in healthy newborn piglets, and in endotoxic newborn piglets. Seventeen piglets were used in this study. The animals were randomised into two groups, a healthy (control) group and an *Escherichia coli* (endotoxic) group. The animals of the endotoxic group received a bolus injection of *E. coli* (1.667 μg/kg), followed by a continuous infusion of *E. coli* (1.667 μg/kg/hr) throughout the experiment. The control group received the same dose of isotonic saline injection and infusion. Approximately 30 minutes thereafter, a sample of blood (0.6 ml) was obtained from the femoral vein catheter prior to injection of the plasma marker. A volume between 0.5 ml and 1.0 ml of the indicator was injected {of approximately 1.0 mg/kg for both plasma markers} via the femoral vein catheter into the bloodstream. The catheter was then flushed clean with an equal volume of isotonic saline. Blood samples (approx 0.6 ml) were withdrawn either into tubes coated with the anticoagulant EDTA {for FITC-Elohaes™} or untreated tubes {for Evans Blue}. As before, following the withdrawal of each sample, the catheter was flushed with an equal volume of isotonic saline. Samples were obtained at various time intervals over a 6 hour period, the majority were collected within the first hour after administration of the plasma marker. Blood samples were then centrifuged at approximately 2500 r.p.m for 10–15 minutes and plasma/serum withdrawn. Blood samples, for determination of Evans Blue distribution space were allowed to clot for 2–3 before centrifugation.

For FITC-Elohaes™ the measurement of fluorescence in plasma was determined as described in Example 2. Plasma free from FITC-Elohaes™ was used as a blank sample, and the procedure was calibrated with known concentrations of the fluorescent polysaccharide.

For the Evans Blue, following centrifugation of the collected blood samples, the serum was removed, ensuring no haemolysis had occurred, and the absorbence measured at 610 nm using a spectrophotometer.

The Volume of Distribution $V_d$ of Evans Blue was determined by plotting the loge values of the first three data points against time and the line of least squares fit derived from linear regression analysis. Concentration of Evans Blue in serum at time zero was therefore ascertained from reverse extrapolation (El-Sayed et al, 1995).

The volume of distribution of FITC-Elohaes™ was calculated as described in Example 2, and the results are shown in Tables 3 and 4.

It will be noted that, (for both healthy and endotoxic piglets), the estimates for plasma volume using FITC-Elohaes™ were lower than those obtained using Evans Blue labelled albumin, but in the endotoxic piglets, the difference was not statistically significant. Likewise, the Volume of Distribution of FITC-Elohaes™ in endotoxic piglets is greater than that for healthy piglets.

TABLE 3

Volume of Distribution of FITC-Elohaes compared with Evans Blue in Healthy Newborn Piglets.

| Piglet No. | FITC Elohaes ™ VD(ml/kg) | Evans Blue VD(ml/kg) |
|---|---|---|
| 1 | 73.1 | 83.5 |
| 2 | 71.2 | * |
| 3 | 78.8 | 86.9 |
| 4 | * | 89.6 |
| 5 | 76.9 | * |
| 6 | 72.3 | 85.1 |

TABLE 3-continued

Volume of Distribution of FITC-Elohaes compared with Evans Blue in Healthy Newborn Piglets.

| Piglet No. | FITC Elohaes ™ VD(ml/kg) | Evans Blue VD(ml/kg) |
|---|---|---|
| 7 | 72.1 | 86.2 |
| Mean | 74.1 | 86.3 |
| STDEV | 3.1 | 1.2 |
| SEM | 2.3 | 1.0 |

\* Values were omitted as they were unbelievably high.
Note: This difference is significant with P < 0.001 [t-test]

TABLE 4

Volume of Distribution of FITC-Elohaes ™ compared to Evans Blue in Endotoxic Newborn Piglets.

| Piglet No. | FITC-Elohaes ™ VD(ml/kg) | Evans Blue VD(ml/kg) |
|---|---|---|
| 8 | 103.3 | 112.9 |
| 9 | 110.5 | 78.3 |
| 10 | 117.9 | * |
| 11 | 122.4 | 98.3 |
| 12 | 111.7 | 140.1 |
| 13 | * | 91.7 |
| 14 | 102.9 | 118.2 |
| 15 | 90.6 | * |
| 16 | 82.3 | * |
| 17 | 73.1 | 111.5 |
| 18 | * | 113.8 |
| MEAN | 101.6 | 108.1 |
| STDEV | 16.5 | 18.7 |
| SEM | 5.5 | 6.6 |

Note: this difference is not statistically significant, with P = 0.46 [t-test]

EXAMPLE 4

A clinical trial was established to compare the plasma volume as determined by FITC-Elohaes™ with the routinely used method of radiolabelled albumin in selected human patients. Outpatients referred for blood volume estimations with radioiodinated albumin and radioactive chromium labelled red cells were tested according to the following protocol:

1. A blood sample was obtained from the patient by venepuncture of the ante-cubital vein, prior to injection of the label
2. Approximately 10.0 ml of FITC-Elohaes™ prepared as in Example 1 was then injected.
3. Approximately 0.15 ml/l of isotonic saline was then injected to flush the fluorescent label into the general circulation.
4. A 5–10 minute mixing period followed, before the first blood sample was obtained.
5. Three blood samples were then obtained over a 30 minute period following injection.
6. The blood samples were then centrifuged at 2500 r.p.m for 10–15 minutes, and the plasma removed.
7. The plasma was then analysed for fluorescent intensity using a Perkin-Elmer Luminescence Spectrophotometer.
8. The data was then plotted semilogarithmically and regressed to determine the fluorescent intensity at time zero (i.e. time of injection).
9. The plasma volume was then calculated from the degree of dilution of the label.

TABLE 6

| PV (ml/kg) Albumin | PV (ml/kg) (FITC-Elohaes ™) |
|---|---|
| RESULTS | |
| 32.8 | 33.7 |
| 39.0 | 42.0 |
| 29.7 | 28.7 |
| 23.0 | 23.6 |
| 15.8 | 27.1 |
| 35.5 | 24.3 |
| 28.0 | 29.6 |
| 32.1 | 27.1 |
| 36.2 | 35.5 |
| 39.2 | 37.6 |
| 37.9 | 33.6 |
| MEAN | |
| 31.8 | 31.2 |
| STDEV | |
| 7.3 | 5.8 |

The results in Table 6 show that, for these patients, the measurement of plasma volume using FITC-Elohaes™ compares favourably with that using labelled albumin. The close agreement between the radiolabelled and FITC-Elohaes™ measurements is believed to be because the patients do not have a disease likely to impair capillary integrity.

EXAMPLE 5

A clinical trial was established to compare the plasma volumes as determined by FITC-Elohaes™ and radiolabelled albumin for two groups of patients; Group I comprising patients with suspected polycythemia, and Group II comprising hospitalised patients who had undergone major surgery in the previous 24 hours and/or who were receiving care in the Intensive Therapy Unit.

For each patient plasma volume was determined using FITC-Elohaes™ at a low dose ($\approx$0.4 mg/kg); at a higher dose ($\approx$4.0 mg/kg) thereof; using radiolodinated albumin; and using radiolabelled red cells.

The measurements for plasma volume using radioiodinated albumin, and radiolabelled red cells followed standard text book techniques.

Low Dose ($\approx$0.4 mg/kg)

Vials containing approximately 5.0 ml of sterile FITC-Elohaes™ solution (5 mg/ml) prepared according to Example 1 were produced. The fluorescent material was taken into a 5.0 ml syringe with appropriate needle attached. The full syringe, and needle were weighed prior to injection.

A blood sample (approx 5.0 ml) was withdrawn by venepuncture of the ante-cubital vein prior to injection of the fluorescent label. An intravenous dose of 5.0 ml (0.4 mg/kg) FITC-Elohaes™ was injected. The empty syringe and needle were re-weighed, in order to calculate the exact volume injected. For every injection, a small amount of the solution was retained. The dose of FITC-Elohaes™ was then flushed into the general circulation with 5.0 ml of sterile isotonic saline solution (9%). The time of injection was noted, and blood samples were taken at appropriate intervals, for example, at 5, 10, and 20 minutes following the time of injection. All blood samples were withdrawn into tubes containing the anticoagulant EDTA.

The blood samples were spun in a bench centrifuge at 2500 r.p.m. for 10–1 5 minutes in order to obtain the plasma. The plasma was removed and assayed for fluorescent intensity as before using a Perkin-Elmer LS-50 Luminescence Spectrometer The fluorescent intensity of the dose was also measured. The loge values of the data was then plotted and regressed to determine the fluorescent intensity at time zero (i.e. time of injection). The volume of distribution was then calculated from the degree of dilution of the label.

High Dose (≈4.0 mg/k)

The procedure was similar to that described above except that 5.0 ml of FITC-Elohaes™ was drawn into a 10 ml syringe followed by 5.0 ml of Elohaes™. The solutions were mixed by agitation before injection into the patient.

Patients with Suspected Polycythaemia—Group I
(i) Dose ≈0.4 mq/kg

Blood volume estimations were performed in 13 patients referred from outpatient clinics with suspected polycythaemia {Group I}. When informed consent was obtained, RCV was estimated by the $^{51}$Cr method and PV estimated by the $^{125}$I-HSA method and the FITC-Elohaest™ method. The volume of distribution {$V_d$} of 125I—was not estimated in patients number 12 & 13 due to shortage of supply of the radiolabel. The individual results for each method and summary statistics are shown below in Table 7. The calculated PV was determined from the following equation:

$$\text{Calculated PV} = \frac{RCV \times (1 - Hct)}{Hct}$$

BV=Calculated PV+RCV

The differences in the results from the three methods of determining PV are compared in Table 8. There is no difference in the $V_d$ for FITC-Elohaes™ and $^{125}$I-HSA but both differ from the PV calculated from RCV and peripheral Hct.

TABLE 8

Differences between FITC-Elohaes ™; $^{125}$I-HSA and Calculated PV in Patients in Group 1

| Patient No. | FITC-Elohaes ™ - Calc PV Difference | $^{125}$I-HSA -Calc PV Difference | $^{125}$I-HSA - FITC-Elohaes ™ Difference |
|---|---|---|---|
| 1 | 7.10 | 6.20 | −0.90 |
| 2 | 12.00 | 9.00 | −3.00 |
| 3 | −3.20 | −2.20 | 1.00 |
| 4 | 4.30 | −7.00 | −11.30 |
| 5 | −2.30 | 8.90 | 11.20 |
| 6 | 5.30 | 4.00 | −1.30 |
| 7 | −4.35 | 0.75 | 5.10 |
| 8 | 2.60 | 3.40 | 0.80 |
| 9 | 1.58 | 3.18 | 1.60 |
| 10 | 2.00 | 6.30 | 4.30 |
| 11 | 4.20 | 4.50 | 0.30 |
| 12 | 8.20 | * | * |
| 13 | 6.60 | * | * |
| Mean | 3.39 | 3.37 | 0.71 |
| ± | ± | ± | ± |
| SEM | 1.31 | 1.43 | 1.67 |
| p-value | 0.024 | 0.041 | 0.680 | p - values were determined by paired (one-sample) t-test {mean = 0}
* = no $^{125}$I-HSA data available (ii) Dose=4.0 mg/kg The $V_d$ of FITC-Elohaes™ {=4.0 mg/kg} and labelled red cells were measured in four other patients with suspected polycythaemia and the results are collected in Table 9. There is still a difference between the $V_d$ of FITC-Elohaes™ and red blood cells but in this smaller sample the difference is no longer significant {p=0.10; paired test}. Again there is no statistically significant difference between the $V_d$ of FITC-Elohaes™ in this group of patients at the two dose levels {mean difference=3 ml/kg; p=0.31, ANOVA}.

TABLE 7

Blood Volume Estimates far Patients in Group 1

| Patient No. | Wt (kg) | Hct | $V_d$ $^{125}$I-HSA (ml/kg) | $V_d$ FITC-Elohaes ™ (ml/kg) | Calc PV (ml/kg) | RCV (ml/kg) | BV (ml/kg) |
|---|---|---|---|---|---|---|---|
| 1 | 89.0 | 0.493 | 32.8 | 33.7 | 26.6 | 25.9 | 52.5 |
| 2 | 79.2 | 0.504 | 39.0 | 42.0 | 30.0 | 30.5 | 60.5 |
| 3 | 74.0 | 0.516 | 29.7 | 28.7 | 31.9 | 34.0 | 65.9 |
| 4 | 96.6 | 0.520 | 15.8 | 27.1 | 22.8 | 21.0 | 43.8 |
| 5 | 66.2 | 0.625 | 35.5 | 24.3 | 26.6 | 44.4 | 71.0 |
| 6 | 79.2 | 0.490 | 28.0 | 29.6 | 24.0 | 23.2 | 47.2 |
| 7 | 124.0 | 0.544 | 32.1 | 27.1 | 31.3 | 37.4 | 68.7 |
| 8 | 69.2 | 0.405 | 36.2 | 35.5 | 32.8 | 22.3 | 55.1 |
| 9 | 75.6 | 0.506 | 39.2 | 37.6 | 36.0 | 36.9 | 72.9 |
| 10 | 48.2 | 0.577 | 37.9 | 33.6 | 31.6 | 43.1 | 74.7 |
| 11 | 77.0 | 0.474 | 32.0 | 31.7 | 27.5 | 24.8 | 52.8 |
| 12 | 74.4 | 0.463 | * | 34.8 | 26.6 | 22.9 | 49.5 |
| 13 | 88.0 | 0.532 | * | 38.5 | 31.9 | 32.1 | 62.0 |
| Mean | 80.1 | 0.511 | 32.6 | 32.6 | 29.2 | 30.7 | 59.9 |
| ± | ± | ± | ± | ± | ± | ± | ± |
| SEM | 4.92 | 0.015 | 2.01 | 1.43 | 1.06 | 2.23 | 2.90 |

Note:
Calc PV and BV determined as above
* = No $^{125}$I-HSA data available.

TABLE 9

Blood Volume Estimations for Group I Patients

| Patient No | Wt (kg) | Hct | $V_d$ FITC-Elohaes ™ (ml/kg) | Calc PV (ml/kg) | RCV (ml/kg) | BV (ml/kg) | 'FITC-Elohaes' ™ -Calc PV Diff |
|---|---|---|---|---|---|---|---|
| 14 | 69.9 | 0.502 | 30.2 | 25.3 | 32.0 | 57.3 | 4.9 |
| 15 | 70.7 | 0.428 | 33.2 | 30.1 | 22.5 | 52.6 | |
| 16 | 94.6 | 0.455 | 23.6 | 20.1 | 16.8 | 36.9 | 3.5 |
| 17 | 108.0 | 0.588 | 31.3 | 31.8 | 32.1 | 63.9 | −0.5 |
| Mean | 85.8 | 0.493 | 29.6 | 26.6 | 25.9 | 52.7 | 2.75 |
| ± | ± | ± | ± | ± | ± | ± | ± |
| SEM | 9.36 | 9.035 | 2.09 | 2.53 | 3.75 | 5.75 | 1.15 |

{Dose of FITC-Elohaes ™ ~ 4.0 mg/kg}

Hospital Patients—Group II

Blood volume parameters were measured in 8 patients who had undergone major surgery in the previous 24 hours and/or were receiving care in ITU {Group II}. The results are collected in Tables 10 and 11. The difference between the $V_d$ of FITC-Elohaes™ and that calculated from red cell distribution is the same as that in the Group I patients but, in this smaller cohort, the difference is not statistically significant. The difference between the $V_d$ of albumin and red cells is much larger in Group II patients but is not statistically significant due to a larger scatter in the data.

TABLE 10

Blood Volume Estimation in Group II Patients

| Patient No. | Wt (kg) | Hct | $V_d$ $^{125}$I-HSA (ml/kg) | $V_d$ FITC-Elohaes ™ (ml/kg) | Calc PV (ml/kg) | RCV (ml/kg) | BV (ml/kg) |
|---|---|---|---|---|---|---|---|
| 1 | 127.0 | 0.217 | 23.0 | 23.6 | 28.7 | 11.0 | 39.7 |
| 2 | 99.0 | 0.380 | 35.1 | 31.8 | 30.0 | 18.7 | 48.7 |
| 3 | 67.0 | 0.411 | 30.7 | 28.4 | 26.8 | 18.7 | 45.5 |
| 4 | 60.0 | 0.356 | 71.5 | 54.5 | 49.0 | 24.8 | 73.8 |
| 5 | 74.5 | 0.439 | 39.9 | 43.3 | 34.2 | 26.7 | 60.9 |
| 6 | 79.2 | 0.270 | 55.2 | 49.4 | 50.8 | 18.8 | 69.6 |
| 7 | 75.0 | 0.488 | 51.9 | 48.6 | 42.2 | 40.2 | 82.4 |
| 8 | 58.1 | 0.488 | 34.0 | 35.4 | 29.8 | 28.4 | 58.2 |
| Mean | 80.0 | 0.389 | 42.7 | 39.4 | 36.4 | 23.4 | |
| ± | ± | ± | ± | ± | ± | ± | ± |
| SEM | 8.10 | 0.030 | 5.58 | 3.95 | 3.38 | 3.10 | 5.24 |

TABLE 11

Difference Between FITC-Elohaes ™; $^{125}$I-HSA

| Patient No. | FITC-Elohaes ™ - Calc PV Difference | $^{125}$I-HSA -Calc PV Difference | $^{125}$I-HSA - FITC-Elohaes ™ Difference |
|---|---|---|---|
| 1 | −5.10 | −5.70 | −0.60 |
| 2 | 1.80 | 5.10 | 3.30 |
| 3 | 1.60 | 3.90 | 2.30 |
| 4 | 5.50 | 22.50 | 17.00 |
| 5 | 9.06 | 5.70 | −3.36 |
| 6 | −1.40 | 4.40 | 5.80 |
| 7 | 6.40 | 9.70 | 3.30 |
| 8 | 5.60 | 4.20 | −1.40 |
| Mean | 2.93 | 6.23 | 3.29 |
| ± | ± | ± | ± |
| SEM | 1.63 | 2.78 | 2.22 |
| p-value | 0.12 | 0.09 | 0.18 | p - values for columns 1 and 3 were determined by a paired t-test as the distribution is Gaussian; p - value for column 2 was determined by a Wilcoxon nonparametric test.

Comparison Between the Two Groups of Patients

Blood volume parameters for the two groups of patients are compared in Table 12. For this comparison, all patients with suspected polycythaemia were placed in a single group as the dose of fluorescently modified starch does not affect the results significantly. As a group, the polycythaemic patients have a higher Hct, as expected, and this is due largely to a contracted PV. This result is recognised using red blood cells or FITC-Elohaes™ to measure PV. The difference is not recognised unequivocally with albumin as plasma label.

A preparation with a similar molecular weight distribution to hmw FITC-Elohaes™ was also produced by ultrafiltration through Centriprep-100 Concentrators™ [Amicon Ltd].

Animal studies with Fluorescent-labelled Polysaccharides

The volume of distribution [$V_d$] and complete pharmacokinetic profiles for the elimination of these three materials

TABLE 12

Comparisan of Blood Volumen Parameters in Group I and Group II Patients

| Patient No. | Wt (kg) | Hct | V $^{125}$1-HSA (ml/kg) | $V_d$ FITC-Elohaes ™ (ml/kg) | Calc PV (ml/kg) | RCV (ml/kg) | BV (ml/kg) |
|---|---|---|---|---|---|---|---|
| Group I | 81.4 ± 4.25 | 0.51 ± 0.013 | 32.6 ± 1.62 | 31.9 ± 1.51 | 28.6 ± 1.00 | 29.5 ± 1.94 | 58.2 ± 2.62 |
| Group II | 80.00 ± 8.10 | 0.39 ± 0.030 | 42.7 ± 5.58 | 39.4 ± 3.95 | 36.4 ± 3.38 | 23.4 ± 3.10 | 59.9 ± 5.23 |
| p-value | 0.870 | <0.001 | 0.070 | 0.030 | 0.008 | 0.100 | 0.750 | p - values were determined by Analysis of Variance {± = SEM}

The combined cohort of patients with suspected polycythaemia {n=17} have a measured PV (calculated from red cell distribution) of 28.6±1.01 ml/kg and a measured RCV of 29.5±1.93 ml/kg. The mean values for PV and RCV, in a healthy population, are quoted as about 40 ml/kg and 30 ml/kg respectively (see Dacie and Lewis, 1995). Therefore, as a group, these patients showed a contracted PV and this reflected in the measured $V_d$ of both albumin {32.6±2.01 ml/kg} and FITC-Elohaes™ {31.9±1.21 ml/kg}. In these patients the $V_d$ of Elohaes™ is indistinguishable from that of albumin and both are significantly different from that calculated from red cell distribution. Increasing the dose of modified starch from about 0.4 mg/kg to 4.0 mg/kg reduces the volume of distribution from 32.6±1.43 ml/kg to 29.6±2.09 ml/kg as predicted from the data gathered with rabbits described above.

EXAMPLE 6

We have prepared samples of FITC-Elohaes™ of higher molecular weight ($M_w$ of greater than 100,000) by molecular sieve chromatography using Sephadex G-200 or by ultrafiltration using Centriprep 100 ultrafilters [Amicon]. Initial studies with three endotoxic piglets using the modified FITC-Elohaes™ show a calculated plasma volume of 67.3±1.47 ml/Kg which is similar to, but significantly lower than, that of healthy piglets using FITC-Elohaes™ prepared as in Example 1.

EXAMPLE 7

Estimating True Plasma Volume, Capillary Permeability/Inflammation and the Extravascular Distribution Space of Small and Large Polysaccharides Preparation of FITC-Elohaes™ with Different Molecular Weight Distributions FITC-Elohaes™ was fractionated by gel-permeation chromatography [Sephadex G-200™ Pharmacia] to separate 33% of the fluorescence as a low molecular weight component and 67% as high molecular weight. The three preparations were named:

Low molecular weight fraction lmw FITC-Elohaes™
FITC-Elohaes™ FITC-Elohaes™
High molecular weight fraction hmw FITC-Elohaes™ was studied in healthy and mature rabbits, healthy and anaesthetised new-born piglets and anaesthetised new-born piglets with an acute septicaemia induced by administration of *Escherichia Coli*. The effect of the original dose on kinetic parameters for Elohaes™ and hmw-Elohaes™ was examined in mature rabbits only.

Physiological Model for Analysis of Elimination Profiles

Figure 1:
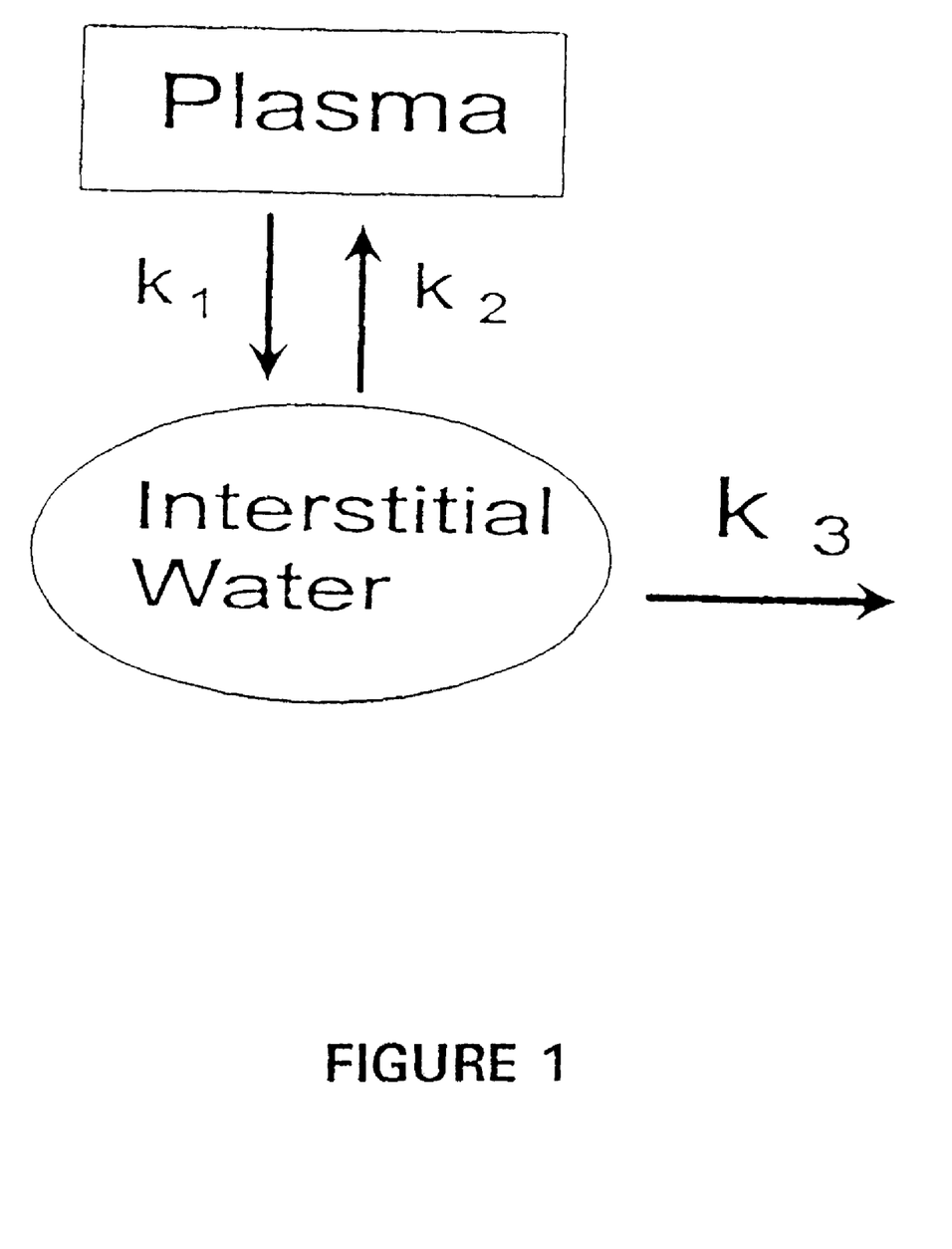
FIG. 1 is a diagram expressing schematically a physiological model for analysis of movement of material between plasma and interstitial water.

The Rowland two-compartment open model was used, with the central compartment being plasma and the peripheral compartment being interstitial water. Elimination was considered to occur from a part of this peripheral compartment. This model is expressed diagrammatically in FIG. 1. In the Figure the rate constants $k_1$ & $k_2$ represent the proportion of material being removed from plasma and returned to plasma from interstitial water respectively. The rate constant $k_3$ is the proportion of material, in interstitial water, being irreversibly eliminated. The parameters of this model, are related to the bi-exponential mathematical model described earlier by:

$$K_2 + K_3 = \frac{(C_1\lambda_2 + C_2\lambda_1)}{(C_1 + C_2)} = A$$

$$k_1 = \lambda_1\lambda_2 - A$$

$$k_3 = \frac{\lambda_1\lambda_2}{k_1}$$

$$k_2 = A - K_3$$

Volume of Distribution ($V_d$) of FITC-Elohaes™ (normal, lmw, and hmw

The $V_d$ of FITC-Elohaes™ clearly depends on the administered dose—the lower the dose the higher the $V_d$. The value of $V_d$ is therefore referred to as the apparent $V_d$ with the true value being realised at high doses as shown in Table 13.

TABLE 13

Effect at dose an $V_d$ on normal FITC-Elohaes ™ on rabbits

| Dose {mg/kg} | No. of Experiments | $V_d$ {ml/kg} & SEM |
|---|---|---|
| 0.15 | 4 | 60.4 ± 1.8 |
| 0.56 | 4 | 52.1 ± 1.8 |
| 1.95 | 5 | 46.7 ± 2.5 |
| 16.60 | 6 | 41.0 ± 3.0 |

Effect of Molecular Weight on $V_d$ of Modified FITC-Elohaes™ in Rabbits

Referring to Table 14, at a given dose, the apparent $V_d$ is clearly effected by the molecular weight of the preparation. Smaller molecules have a larger apparent volume of distribution.

TABLE 14

$V_d$ for FITC-Elohaes ™ and its High Molecular Weight Components

| Preparation | Dose [mg/kg] | $V_d$ |
|---|---|---|
| FITC-Elohaes ™ [n = 8] | 0.10 ± 0.019 | 59.5 ± 1.20 |
| lmw-FITC-Elohaes ™ [n = 3] | 0.07 ± 0.005 | 68.8 ± 4.07 |
| hmw-FITC-Elohaes ™ [n = 5] | 0.12 ± 0.012 | 44.8 ± 0.80 |
| P-value | 0.35 | <0.0001 |

P-values are by ANOVA [MINITAB]

Effect of Endotoxaemia and Molecular Weight on $V_d$ of FITC-Elohaes™ and hmw-FITC-Elohaes™ in Piglets Referring to Table 15, the $V_d$ of FITC-Elohaes™, but not of hmw-FITC-Elohaes™, is increased in the endotoxic group.

TABLE 15

$V_d$ of FITC-Elohaes ™ & hmw-FITC-Elohaes ™ in Control and Endotoxic Piglets.

| Compound → Experimental Group ↓ | FITC-Elohaes ™ | hmw-FITC-Elohaes ™ | p-value |
|---|---|---|---|
| Control | 74.1 ± 1.2 | 67.4 ± 2.7 | 0.15 |
| Endotoxic | 101.6 ± 5.5 | 64.8 ± 3.5 | 0.0001 |
| p-value | 0.0013 | 0.58 | |

Dose = 1.0 mg/kg.p-value are by ANOVA

Kinetic Constants for Elimination of FITC-Elohaes™

Referring to Table 16, the kinetics of elimination of FITC-Elahaes™ is unaffected by the initial dose.

TABLE 16

Effect of dose on kinetic constants for elimination of FITC-Elohaes ™ in rabbits

| Dose (mg/kg) | N | $k_1(min^{-1})$ | $k_2(min^{-1})$ | $k_3(min^{-1})$ |
|---|---|---|---|---|
| 0.15 | 4 | 0.0163 ± 0.0046 | 0.0140 ± 0.0048 | 0.00128 ± 0.00044 |
| 0.56 | 4 | 0.0122 ± 0.0024 | 0.0085 ± 0.0017 | 0.00090 ± 0.00007 |
| 1.95 | 5 | 0.0199 ± 0.0052 | 0.096 ± 0.0054 | 0.00124 ± 0.00029 |
| 16.63 | 6 | 0.0145 ± 0.0013 | 0.0107 ± 0.0017 | 0.00120 ± 0.00016 |
| Mean | 19 | 0.0157 ± 0.0017 | 0.0133 ± 0.0019 | 0.00116 ± 0.00012 |
| P-value | 4 | 0.540 | 0.200 | 0.772 |

Pharmacokinetic Constants for Model. P-values were determined by ANOVA

Pharmacokinetic Constants for Model. P-values were Determined by ANOVA

Referring to Tables 17 and 18, induced endotoxaemia does not appear to affect the kinetics of FITC-Elohaes™ nor hmw-FITC-Elohaes™ elimination. The ratio of $k_1/k_2$ represents the relative amounts of FITC-Elohaes™ in interstitial water and plasma at equilibrium. This is also unaffected by endotoxaemia.

TABLE 17

Effect of endotoxaemia on kinetic constants for FITC-Elohaes ™ elimination in piglets.

| Experimental Conditions | N | $k_1(min^{-1})$ | $k_2(min^{-1})$ | $k_3(min^{-1})$ | $k_1/k_2$ |
|---|---|---|---|---|---|
| Control | 4 | 0.036 ± 0.013 | 0.029 ± 0.008 | 0.0046 ± 0.0014 | 1.19 ± 0.17 |
| Endotoxic | 9 | 0.025 ± 0.004 | 0.025 ± 0.005 | 0.0046 ± 0.0003 | 1.09 ± 0.06 |
| p-value | | 0.48 | 0.67 | 0.99 | 0.51 |

Rate Constants for Elimination of FITC-Elohaes ™ Control and Experimental Groups of Piglets [dose = 1.0 mg/kg] p-values were determined by ANOVA.

TABLE 18

Effect of endotoxaemia on kinetic constants for hmw-FITC-Elohaes ™ elimination in piglets.

| Experimental Conditions | N | $k_1(min^{-1})$ | $k_2(min^{-1})$ | $k_3(min^{-1})$ | $k_1/k_2$ |
|---|---|---|---|---|---|
| Control | 3 | 0.029 ± 0.012 | 0.038 ± 0.012 | 0.0048 ± 0.0003 | 0.74 ± 0.13 |
| Endotoxic | 6 | 0.041 ± 0.014 | 0.047 ± 0.013 | 0.0054 ± 0.0006 | 0.84 ± 0.16 |
| p-value | | 0.50 | 0.64 | 0.42 | 0.71 |

Rate Constants for Elimination of Fhmw FITC-Elohaes ™ Control and Experimental Groups of Piglets [dose = 1.0 mg/kg]. p-values were determined by ANOVA The Effect of Molecular Weight on the Kinetic Constants for FITC-Elohaes™ and hmw-FITC-Elohaes™ Elimination in Piglets.

All data from rabbits were pooled and coded by the molecular weight of the administered fluorescent starch. Similarly all data from piglets was pooled and coded by the same parameter. Results of ANOVA are summarised below.

TABLE 19

Elimination constants for FITC-Elohaes ™, lmw-FITC Elohaes ™ and hmw-FITC-Elohaes ™, in Rabbits

| Experimental Conditions | N | $k_1(min^{-1})$ ± SEM | $k_2(min^{-1})$ ± SEM | $k_3(min^{-1})$ ± SEM | $k_1/k_2$ ± SEM |
|---|---|---|---|---|---|
| lmw-FITC-Elohaes ™ | 3 | 0.0148 ± 0.0053 | 0.0053 ± 0.0006 | 0.0014 ± 0.0001 | 2.86 ± 0.27 |
| FITC-Elohaes ™ | 19 | 0.0157 ± 0.0017 | 0.0133 ± 0.0019 | 0.0012 ± 0.0001 | 1.32 ± 0.08 |
| hmw-FITC-Elohaes ™ | 8 | 0.0119 ± 0.0014 | 0.0156 ± 0.0039 | 0.0015 ± 0.0003 | 0.96 ± 0.16 |
| p-value One-way ANOVA | | 0.39 | 0.25 | 0.38 | <0.001 |

TABLE 20

Elimination constants for FITC-Elohaes ™ and hmw-FITC-Elohaes ™ in new-born piglets

| Experimental Conditions | N | $k_1(min^{-1})$ ± SEM | $k_2(min^{-1})$ ± SEM | $k_3(min^{-1})$ ± SEM | $k_1/k_2$ ± SEM |
|---|---|---|---|---|---|
| FITC-Elohaes ™ | 13 | 0.029 ± 0.005 | 0.026 ± 0.004 | 0.0046 ± 0.0004 | 1.12 ± 0.06 |
| hmw-FITC-Elohaes ™ | 9 | 0.037 ± 0.010 | 0.044 ± 0.009 | 0.0052 ± 0.0004 | 0.80 ± 0.11 |
| p-value One-way ANOVA | | 0.39 | 0.07 | 0.36 | <0.02 |

The distribution of polysaccharide is biased towards interstitial water when the molecular weight distribution of the material is shifted to low values.

Upon review of this data we have made two findings. Firstly, a minor proportion of molecules of FITC-Elohaes™ are small enough to occupy relatively small pores in capillary walls and the flow of material through these pores is much slower than that for the majority of molecules which flow through very large pores with no retardation. The larger molecules are swept away from the smaller pores by blood flow along the capillary. An increase in the initial loss of small molecules would indicate an increase in the number and/or size of small pores and a concomitant increase in capillary permeability. This is consistent with modern theories of a bimodal size selectivity of the harrier partitioning blood from lymph. This phenomenon would explain the effect of concentration and molecular weight on the apparent $V_d$. The true $V_d$ is therefore realised at high doses of FITC-Elohaes™ (when the proportion of the total molecules adsorbed into small pores is small) or with hmw-FITC-Elohaes™, which does not have molecules small enough to occupy the smaller pores in capillary walls.

The same results would be obtained if the small molecules of FITC-Elohaes™ are bound to receptors on endothelial cell surfaces. In this case any increase may be interpreted as an upregulation of these receptors by inflammation that might accompany an impairment in capillary integrity and an increase in capillary permeability.

Secondly, the kinetic constants, used here to define the elimination profiles of fluorescent. labelled hydroxyethylstarch, are affected differently by experimental variations such as the size range of the macromolecule and the presence or absence of an experimentally induced endoxaemia. It seems particularly surprising that the rate of removal [k1] of such large molecules is insensitive to their size, even in the presence of visible tissue oedema. Changes in the relative amounts of polysaccharide in extravascular water and plasma (i.e. $k_1/k_2$), at equilibrium, is however effected by experimental conditions. This is almost certainly caused by changes in $k_2$ rather than $k^{hd\ 1}$ and it is influenced by the size distribution of the administered material but not the dose nor the presence of oedema. The large molecules are thus returned to plasma at a faster rate than smaller molecules. This is unlikely to reflect size selectivity by pores as it is difficult to envisage pores that allow large molecules easier access than smaller molecules of the same general properties.

Consider the situation where $k_3<<k_2$. At equilibrium the rate of flow of FITC-Elohaes™ $\{Y_p\}$ out of plasma will be balanced by the rate of return of FITC-Elohaes™ $\{Y_p\}$ from interstitial water:

$$\frac{dY_p}{dt} = 0 = k_1 Y_p - k_2 Y_i$$

It follows that $$k_1 Y_p = k_2 Y_i$$

and $$\frac{k_1 Y_p}{V_p} = \frac{K_2 Y_i}{V_p} = \frac{K' Y_i}{V_i}$$

and the apparent rate constant $k_2$ is related to the real rate constant k' by:

$$k_2 = \frac{k' V_p}{V_i}$$

It can be seen that $k_1$ indicates the proportion of plasma that flows into lymph, through large pores, in one minute and k' is the proportion of interstitial water being returned to plasma in a minute. Hence the value of $k_2$ is an indirect measure of the volume of interstitial water which is available to a macromolecule and for the production of lymph. As the interstitial space can be considered as a molecular sieve, akin to materials like Sephadex™, then the proportion of the total water which is available to any molecule will be inversely related to its size. It follows that the value $k_2$, for a macromolecule, will be directly related to its size—there is no experimental evidence of any relationship between the size of the molecule and the value of $k_1$. Hence, because of individual variations in rate constants between individual animals, the ratio $k_1/k_2$ seems to be a better guide to true differences in $k_2$ between different molecules. These ratios are not effected by the induced endotoxaemia which suggests that the extra interstitial water is part of the gel-matrix of extracelluar space and not accessible to molecules of FITC-Elohaes™ nor for the production of lymph.

Accordingly our results presented above suggest that the extravascular $V_d$ of FITC-Elohaes™, which is reflected in the value of $k_2$, is inversely related to the molecular size of the polysaccharide. The measured $V_d$ of FITC-Elohaes™, calculated from the initial concentration, is also inversely related to the size of the molecules. However there is a paradox—the two values for the $V_d$ are not directly comparable. The value of $k_2$, and hence the true extravascular $V_d$, is not affected by the dose nor by the presence of tissue oedema—the measured $V_d$ depends on both of these experimental variables. This anomaly is entirely consistent with a two-pore theory of plasma filtration to produce lymph. The bulk transport of molecules, as large as those found in FITC-Elohaes™, is through large pores with a radius of about 40 nm or more. These figures are therefore a measure of the minimum rate of filtration of plasma into interstitial water—they do not measure flow through small pores.

Accordingly FITC-Elohaes™, suitably fractionated may be used to measure three separate but inter-related parameters:

1) The $V_d$ of hmw-FITC-Elohaes™ is a measure of true circulating plasma volume {PV}.
2) The ratio between the $V_d$ of hmw-FITC-Elohaes™ and FITC-Elohaes™ {$V_d$/PV} is a measure of capillary permeability/inflammation.
3) The ratio of $k_1/k_2$, for FITC-Elohaes™, measures the relative volume of plasma and interstitial water which is accessible to molecules of FITC-Elohaes™.

In the absence of a complete elimination profile, e.g. in human patients, the ratio of $k_1/k_2$ can be accessed from the ratio of the amount of FITC-Elohaes™ in plasma to that in extravascular water at equilibrium. This ratio can be estimated from $[(C_0-C_{60})/C_{60}]$ where $C_{60}$ is the concentration after 60 minutes and $C_0$ is the concentration at zero time. The following Table 21 summarises the information from piglets according to these three principles.

TABLE 21

Intravascular and extravascular distribution of FITC-Elohaes ™ in healthy and septic piglets.

| | True PV {ml/kg} | $V_d$/PV | $k_1/k_2$ | $C_{60}/(C_0-C_{60})$ |
|---|---|---|---|---|
| Control Group | 67.4 ± 2.7 | 1.10 ± 0.02 | 1.19 ± 0.17 | 1.18 ± 0.33 |
| Experimental Group | 64.8 ± 3.5 | 1.51 ± 0.05 | 1.09 ± 0.06 | 0.92 ± 0.05 |
| p-value | 0.58 | 0.001 | 0.62 | 0.49 |

EXAMPLE 8

Determining Plasma Volume and Capillary Permeability

1. A low dose (typically 0.4 mg/kg) of lmw-FITC-Elohaes™ is administered and its concentration in plasma estimated after 5 min [$C_5$], 10 min [$C_{10}$], 20 min [$C_{20}$] and 60 min [$C_{60}$]. The first three points are used to determine the concentration at time zero [$C_0$] and hence the apparent volume of distribution [$V_d$]=Dose/$C_0$.

The ratio of $[(C_0-C_{60})/C_{60}]$ estimates the relative estimated amounts of low molecular weight material in interstitial water and plasma at equilibrium.

2. A high dose (typically 4.0 mg/kg (i.e about ten times the amount of fluorescence in the first dose) of hmw-FITC-Elohaes™ is administered. Its concentration in plasma is estimated after 5 min [$C_5$], 10 min [$C_{10}$], 20 min [$C_2$] and 60 min [$C_{60}$]. The first three points are used to determine the concentration at time zero [$C_0$] and hence the true circulating plasma volume [PV]. The ratio $(C_0-C_{60})/C_{60}$ estimates the relative amounts of high molecular weight material in interstitial water and plasma at equilibrium. The ratio of $V_d$/PV is an estimate of the permeability of the capillaries to small molecules of polysaccharide.

Fewer combinations of these procedures can be used to yield less information. Hence points at 60 min can be excluded to obtain estimates only of PV and capillary permeability. Again measurements can be made after 5 min only and a general correction applied to obtain the concentration at zero time. The rate of removal of the macromolecules is surprisingly insensitive to changes in experimental conditions and this sort of general correction may prove adequate.

The label of lmw-FITC-Elohaes™ could be different from that of hmw-FITC-Elohaes™. Both compounds could then be administered simultaneously to speed up the procedures.

The invention also extends to methods or apparatus in which the macromolecular materials are labelled or detected after introduction into the blood stream.

What is claimed is:

1. A method of determining the presence or onset of capillary permeability of a subject which comprises:
   introducing into the blood stream of the subject a dose of a first labelled relatively low molecular weight macromolecular material having a substantial portion of molecules with a molecular weight of less than 100,000 Da,
   taking at least one blood sample after said introduction;
   determining the amount and/or concentration of said first labelled macromolecular material at one or more intervals after introduction thereof, and using the determined concentrations to deduce the concentration at time zero, and at: equilibrium respectively of said first labelled macromolecular material thereby to determine a measure of the apparent plasma volume;
   introducing into the bloodstream of the subject a dose of a second labelled relatively high molecular weight macromolecular material having a substantial proportion of molecules with a molecular weight of greater than 100,000 Da;
   taking at least one blood sample after said introduction;
   determining the amount and/or concentration of said second labelled macromolecular material at one or more intervals after introduction thereof and using the determined concentrations to deduce the concentration at time zero and equilibrium respectively of said second labelled macromolecular material, thereby to determine a measure of the true plasma volume;
   comparing the determined measuring of apparent and true plasma volume to indicate the presence or onset of capillary leakage.

2. A method according to claim 1, wherein said macromalecular materials comprise colloid or crystalloid materials.

3. A method according to claim 2, wherein said macromolecular materials comprises modified or unmodified polysaccharide.

4. A method according to claim 2, wherein said second labelled macromolecular material comprises a high molecular weight fraction of a polydisperse colloid or crystalloid material.

5. A method according to claim 4, wherein said first labelled macromolecular material comprises a low molecular weight fraction of a polydisperse colloid or crystalloid material.

6. A method according to claim 4, wherein said first labelled macromolecular material comprises a polydisperse colloid or crystalloid material.

7. A method according to claim 1, wherein said high molecular weight macromolecular material contains a substantial proportion of molecules having a molecular weight greater than 100,000 Da.

8. A method according to claim 7, wherein the high molecular weight fraction has a weight average molecular weight ($MW_w$) of at least 100,000 Da.

9. A method according to claim 1, wherein said macromolecular materials comprise hydroxyethyl starch.

10. A method according to claim 1, wherein the dose of said first labelled macromolecular material is lower than the dose of said second labelled macromolecular material.

11. A method according to claim 10, wherein the dose of said second labelled macromolecular material is between 6 and 14 times that of said first labelled macromolecular material, and preferably about 10 times.

12. A method according to claim 10, wherein the dose of said high molecular weight material is greater than 2.0 mg/kg.

13. A method according to claim 1, wherein the values of the concentrations of said first labelled macromolecular material at time zero and at equilibrium are used to determine the relative amounts of said first labelled material within and outside the capillary.

14. A method according to claim 1, wherein the values of the concentrations of said second labelled macromolecular material at time zero and at equilibrium are used to determine the relative amounts of said second labelled material within and outside the capillary.

15. A method according to claim 1, wherein the concentrations at time zero of sold first and said second labelled macromolecular materials are compared to determine the presence or onset of capillary leakage.

16. Apparatus for determining the presence or onset of capillary permeability of a subject which comprises:

means for introducing into the blood stream of the subject a dose of a first labelled relatively low molecular weight macromolecular material having a substantial proportion of molecules with a molecular weight of less than 100,000 Da;

means for taking at least one blood sample after said introduction;

means for determining the amount and/or concentration of said first labelled macromolecular material;

means for introducing into the blood stream of the subject a dose of a second labelled relatively high molecular weight macromolecular material having a substantial proportion of molecules with a molecular weight of greater than 100,000 Da;

means for taking at least one blood sample after said introduction;

means for determining the amount and/or concentration of said second labelled high molecular weight macromolecular material;

processing means for using the relative determined concentrations and/or amounts of said labelled materials to indicate the presence or onset of capillary leakage.

17. A method according to claim 1, wherein said first labelled macromolecular material is introduced into the blood stream before the introduction of said second labelled macromolecular material.

18. A method according to claim 10, wherein the dose of said high molecular weight material is about 4.0 mg/kg.

* * * * *